United States Patent [19]

Ohno et al.

[11] 4,061,769
[45] Dec. 6, 1977

[54] METHOD AND COMPOSITION FOR TREATING HYPERTENSION

[75] Inventors: Masaji Ohno; Mutsuo Kataoka, both of Kamakura, Japan

[73] Assignee: Zaidan Hojin Biseibutsu Kagaku Kenkyu Kai, Tokyo, Japan

[21] Appl. No.: 672,594

[22] Filed: Apr. 1, 1976

Related U.S. Application Data

[62] Division of Ser. No. 363,559, May 24, 1973, Pat. No. 3,963,756.

[30] Foreign Application Priority Data

May 24, 1972 Japan .................................. 47-50776

[51] Int. Cl.² .................... A61K 31/35; A61K 31/36
[52] U.S. Cl. .................................... 424/283; 424/282
[58] Field of Search ............................. 424/283, 282

[56] References Cited

PUBLICATIONS

*Chemical Abstracts,* vol. 50, 980e.

*Primary Examiner*—Frederick E. Waddell
*Attorney, Agent, or Firm*—Haight & Huard

[57] ABSTRACT

New compounds of the formula

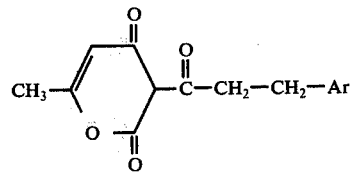

wherein Ar is selected from the group consisting of phenylethyl, furyl, methylfuryl, thienyl, pyrrolyl, naphthyl, hydroxynaphthyl, and phenyl substituted by at least one member selected from the group consisting of halogen, hydroxyl, cyano, trifluoromethyl, alkyl of 1-4 carbon atoms, alkoxy of 1-4 carbon atoms, carbamoyl, amino of the formula —NR'R", alkoxycarbonyl of the formula —CO—OR' wherein R' and R" are each alkyl of 1-4 carbon atoms, and alkylenedioxy of the formula —O—R'"—O— wherein R'" is alkylene of 1-4 carbon atoms, provided that said substituted phenyl is not 3,4-di-methoxyphenyl, and the addition salts thereof with the cation of an organic or inorganic base inhibit the enzyme activities of tyrosine hydroxylase and dopamine β-hydroxylase and are useful chemotherapeutic agents in the treatment of essential hypertension.

14 Claims, No Drawings

METHOD AND COMPOSITION FOR TREATING HYPERTENSION

This is a division of application Ser. No. 363,559 filed May 24, 1973, now U.S. Pat. No. 3,963,756.

BACKGROUND OF THE INVENTION

This invention relates to new derivatives of 6-methyl-2H-pyran-2,4(3H)-dione and more particularly to derivatives of 3-hydrocinnamoyl-6-methyl-2H-pyran-2,4(3H)-dione which are useful hypotensive agents, as well as to processes for their preparation and use and to pharmaceutical compositions containing one or more of the compounds as a hypotensive agent.

Many attempts have been made to synthesize new chemical compounds which are biologically active and especially useful as medicines. An object of this invention is to provide new compounds which are useful as hypotensive agent and to provide a simple and efficient process for the production of such new hypotensive compounds.

It is known that 3-hydrocinnamoyl-6-methyl-2H-pyran-2,4(3H)-dione exhibits a weak antibacterial and antifungal activity, as has been described in "Chemical Abstracts" 50, 980e. 3-(3,4-dimethoxyhydrocinnamoyl)-6-methyl-2H-pyran-2,4(3H)-dione is known, and has been described in "Chemical Abstracts" 50, 14695c.

OBJECTS OF THE INVENTION

Accordingly, it is an object of the present invention to provide new derivatives of 6-methyl-2H-pyran-2,4(3H)-dione, intermediates therefor and methods for their preparation.

Another object of the present invention is to provide pharmaceutical compositions suitable for the treatment of essential hypertension.

A further object of this invention is to provide a process for lowering blood pressure in animals, including man.

An additional object of this invention is to provide a process for inhibiting the enzymatic activity of tyrosine hydroxylase.

Yet another object of the present invention is to provide a process for inhibiting the enzymatic activity of dopamine β-hydroxylase.

Other objects and advantages of this invention will become apparent to those skilled in the art upon further study of the specification and appended claims.

SUMMARY OF THE INVENTION

Briefly, the above and other objects are attained in one aspect of the present invention by providing new compounds selected from the group consisting of 6-methyl-2H-pyran-2,4(3H)-diones of the Formula I

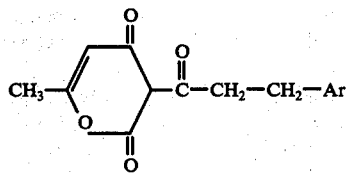

and the pharmaceutically acceptable salts thereof, wherein Ar is as defined hereinbelow.

In another aspect of this invention, pharmaceutical compositions are provided comprising a hypotensively effective amount of a compound of Formula I; 3-hydrocinnamoyl-6-methyl-2H-pyran-2,4(3H)-dione; 3-(3,4-dimethoxyhydrocinnamoyl)-6-methyl-2H-pyran-2,4(3H)-dione; or the pharmaceutically acceptable salts thereof.

In yet another aspect of this invention, the enzyme activity of tyrosine hydroxylase and/or dopamine β-hydroxylase is inhibited by contact with an enzyme-inhibiting amount of a compound of Formula I; 3-hydrocinnamoyl-6-methyl-2H-pyran-2,4(3H)-dione; 3-(3,4-dimethoxyhydrocinnamoyl)-6-methyl-2H-pyran-2,4(3H)-dione; or the pharmaceutically acceptable salts thereof

DETAILED DISCUSSION

We have now discovered that these two known compounds also exhibit an activity of lowering the blood pressure in mammals and are thus useful as hypotensive agents. As a result of extensive research aimed at providing compounds which are even more useful hypotensive agents than the above-mentioned two known compounds, we have now succeeded in synthesizing new derivatives of 6-methyl-2H-pyran-2,4(3H)-dione of the general formula

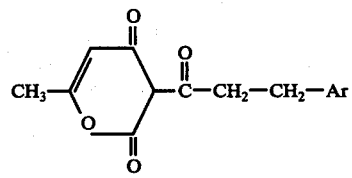

wherein Ar is monovalent carbocyclic or heterocyclic aryl, other than unsubstituted phenyl or 3,4 dimethoxyphenyl, containing 1 or 2 separate or fused rings, 5–10 ring atoms and 0–4, preferably 0–2 and especially 0–1 oxygen, nitrogen or sulfur hetero ring atoms. Preferred carbocyclic aryl groups are substituted phenyl as defined hereinbelow and naphthyl; preferred heterocyclic aryl groups are five membered rings having 1–2, preferably 1 oxygen, nitrogen or sulfur hetero ring atoms, e.g., imidazolyl, oxazolyl, thiazoyl, and pyrazolyl; preferred are furyl, thienyl and pyrrolyl. Moreover, we have found that these new derivatives of 6-methyl-2H-pyran-2,4(3H)-dione of the above general formula [I] exhibit a remarkable effect as a blood-pressure reducing agent, that is, a hypotensive agent. These compounds have the useful activities of reducing blood pressure in animals, a low toxicity and a high biochemical activity of inhibiting the actions of both tyrosine hydroxylase and dopamine β-hydroxylase, as well as exhibiting a high biochemical activity in inhibiting the biosynthesis of norepinephrine.

According to a generic, first aspect of the present invention, therefore, there is provided as new compound a derivative of 6-methyl-2H-pyran-2,4(3H)-dione of the general formula:

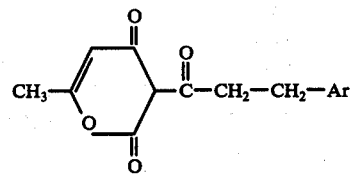

in which Ar stands for an aromatic or heterocyclic group selected from a substituted phenyl, a substituted or unsubstituted furyl, a substituted or unsubstituted thienyl, a substituted or unsubstituted pyrrolyl, a substituted or unsubstituted naphthyl and a substituted or unsubstituted phenylethyl, provided that said substituted phenyl is not 3,4-di-methoxyphenyl. Suitable examples of Ar shown in the above general formula [I] include but are not limited to 2-chlorophenyl, 3-chlorophenyl, 4-chlorophenyl, 2-bromophenyl, 3-bromophenyl, 4-bromophenyl, 2-fluorophenyl, 3-fluorophenyl, 4-fluorophenyl; 2-hydroxyphenyl, 3,-hydroxyphenyl, 4-hydroxyphenyl; 2-cyanophenyl, 3-cyanophenyl, 4-cyanophenyl; 3-trifluoromethyl, 4-trifluoromethyl; 2-methylphenyl, 3-methylphenyl, 4-methylphenyl; 2-ethylphenyl, 3-ethyl-phenyl, 4-ethylphenyl, 4-isopropylphenyl; 2-methoxyphenyl, 3-methoxyphenyl, 4-methoxyphenyl, 2-ethoxyphenyl, 3-ethoxyphenyl, 4-ethoxyphenyl; 4-carbamoylphenyl; 4-dimethylaminophenyl; 4-ethoxycarbonylphenyl; 3,4-dichlorophenyl, 2,4-dichlorophenyl, 2,6-dichlorophenyl; 2,4-dihydroxyphenyl, 2,5-dihydroxyphenyl; 3-ethyl-4-hydroxyphenyl; 2-hydroxy-3-methoxyphenyl, 3-hydroxy-4-methoxyphenyl, 4-hydroxy-3-methoxyphenyl; 2-hydroxy-3-ethoxyphenyl; 2,3-di-methoxyphenyl, 2,4-di-methoxyphenyl; 2-hydroxy-4-methoxycarbonylphenyl; 3,4-dihydroxyphenyl; 3,4-methylenedioxyphenyl; 3,5-dichlorophenyl; 2,4,6-trimethylphenyl; 4-hydroxy-3,5-dimethoxyphenyl; furan-2-yl, 5-methylfuran-2-yl; thien-2-yl; pyrrol-2-yl; α-naphthyl, β-hydroxy-α-naptyl and phenylethyl. Of these, preferred are 4-chlorophenyl, 2-hydroxyphenyl, 3-hydroxyphenyl, 4-hydroxyphenyl, 4-cyanophenyl, 2-methoxyphenyl, 3-methoxyphenyl, 4-methoxyphenyl, 3,4-methylenedioxyphenyl and 2,4-dichlorophenyl.

According to a preferred embodiment of the first aspect of the present invention, therefore, there is provided a derivative of 6-methyl-2H-pyran-2,4(3H)-dione of the general formula

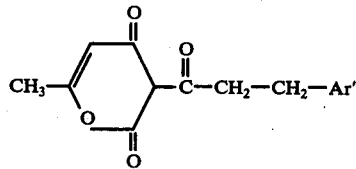

wherein Ar' is a mono-substituted or di-substituted phenyl group of the formula:

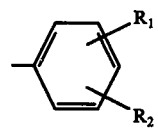

in which $R_1$ and $R_2$ can be the same or different and are each a hydrogen atom, a halogen atom, hydroxyl, cyano, trifluoromethyl, a lower alkyl of 1–4 carbon atoms, a lower alkoxyl of 1–4 carbon atoms, carbamoyl — $CONH_2$, a substituted amino group —NR'R" or an alkoxycarbonyl group of the formula —CO—OR' where R' and R" may be the same or different and are each lower alkyl of 1—4 carbon atoms, provided that both of $R_1$ and $R_2$ are neither hydrogen atoms at the same time nor 3,4-dimethoxy groups; or $R_1$ and $R_2$ together form an alkylenedioxy chain of the formula —O—R'"—O— where R'" is a lower alkylene or 1—4 carbon atoms; or wherein Ar' is a tri-substituted phenyl of the formula:

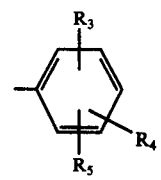

in which $R_3$, $R_4$ and $R_5$ can be the same or different and are each a halogen atom, hydroxyl, a lower alkyl of 1–4 carbon atoms or a lower alkoxy of 1–4 carbon atoms; or wherein Ar' is a α-naphthyl, β-hydroxy-α-naphthyl or phenylethyl or a heterocyclic group, e.g. furyl, methylfuryl, thienyl or pyrrolyl.

According to a more particularly preferred embodiment of the first aspect of the present invention, there is provided a derivative of 3-hydrocinnamoyl-6-methyl-2H-pyran-2,4(3H)-dione of the general formula:

wherein $R_1$ and $R_2$ can be the same or different and are each a hydrogen atom, a halogen atom, hydroxy, cyano, trifluoromethyl, a lower alkyl of 1–4 carbon atoms, a lower alkoxy of 1–4 carbon atoms, carbamoyl — $CONH_2$, a substituted amino group of the formula —NR'R" and an alkoxycarbonyl group of the formula —CO—OR' where R' and R" can be the same or different and are each a lower alkyl of 1–4 carbon atoms, provided that both of $R_1$ and $R_2$ are neither hydrogen atoms at the same time nor 3,4-dimethoxy groups; or $R_1$ and $R_2$ together form an alkylenedioxy chain of the formula —O—R'"—O— where R'" is a lower alkylene of 1—4 carbon atoms, e.g. methylene or 1,1-ethylene (>$CHCH_3$).

Preferred compounds of the invention are those compounds of Formula I meeting one or more of the following criteria:

a. Those in which Ar is phenyl substituted by at least one lower alkyl of 1-4 carbon atoms;

b. Those in which Ar is phenyl substituted by at least one hydroxy or lower alkoxy of 1-4 carbon atoms;

c. Those in which Ar is phenyl substituted by at least one alkylenedioxy of 1-4 carbon atoms;

d. Those in which Ar is phenyl substituted by at least one halogen, preferably chlorine;

e. Those in which Ar is phenyl substituted by alkoxycarbonyl of 2-5 carbon atoms;

f. Those in which Ar is phenyl substituted by an amino group of the formula —NR'R" wherein R' and R" are each alkyl of 1-4 carbon atoms;

g. Those in which Ar is phenyl substituted by cyano;

h. Those in which Ar is phenyl substituted by trifluoromethyl;

i. Those in which Ar is phenyl substituted by carbamoyl;

j. Those in which Ar is furyl unsubstituted or substituted by methyl.

Among the new compounds of the present invention, the following compounds are remarkably effective hypotensive agents:

3-(4-methoxyhydrocinnamoyl)-6-methyl-2H-pyran-2,4(3H)-dione;
3-(2-hydroxyhydrocinnamoyl)-6-methyl-2H-pyran-2,4(3H)-dione;
3-(3-hydroxyhydrocinnamoyl)-6-methyl-2H-pyran-2,4(3H)-dione;
3-(4-hydroxyhydrocinnamoyl)-6-methyl-2H-pyran-2,4(3H)-dione;
3-(3,4-dichlorohydrocinnamoyl)-6-methyl-2H-pyran-2,4(3H)-dione;
3-(4-chlorohydrocinnamoyl)-6-methyl-2H-pyran-2,4(3H)-dione;
3-(3,4-methylenedioxyhydrocinnamoyl)-6methyl-2H-pyran-2,4(3H)-dione;
3-(3-chlorohydrocinnamoyl)-6-methyl-2H-pyran-2,4(3H)-dione;
3-(5-phenylvaleryl)-6-methyl-2H-pyran-2H-pyran-2,4(3H)-dione;
3-(3-hydroxy-4-methoxyhydrocinnamoyl)-6-methyl-2H-pyran-2,4(3H)-dione;
3-(2,4-dichlorohydrocinnamoyl)-6-methyl-2H-pyran-2,4(3H)-dione;
3-(4-methylhydrocinnamoyl)-6-methyl-2H-pyran-2,4(3H)-dione;
3-[3-(2-furyl)propanoyl]-6-methyl-2H-pyran-2,4(3H)-dione; and
3-(4-methoxycarbonylhydrocinnamoyl)-6-methyl-2H-pyran-2,4(3H)-dione.

The compounds of this invention exist in the free form and as salts with one or more cations of organic or inorganic bases, e.g. with a physiologically acceptable base.

In the presence of a cation $M^{n+}$, the compounds of Formula I form salts of the Formula I(c):

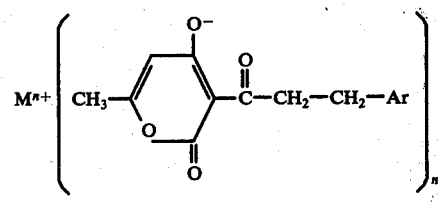

wherein $M^{n+}$ is an organic or inorganic cation having a valence $n$ of 1-3. Suitable pharmaceutically acceptable cations include but are not limited to monovalent metal cations of the alkali metals, e.g. sodium or potassium; divalent metal cations of the alkaline earth metals, e.g. calcium or magnesium; and trivalent cations, e.g. aluminum. The salts can be simple, complex or mixed, and the toxic salts can be used for isolation and/or characterization procedures. Together with a metal cation $M^{n+}$, the compound of the formula forms a salt of the formula:

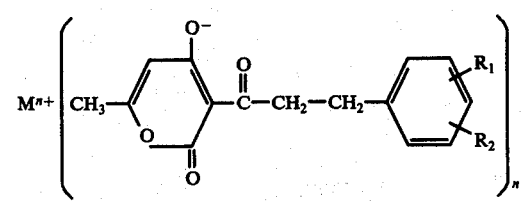

wherein $M^{n+}$ is a pharmaceutically acceptable cation of the valence $n$, e.g., an alkali metal cation or an alkaline earth metal cation, and $R_1$ and $R_2$ are defined above.

The new derivatives of 6-methyl-2H-pyran-2,4(3H)-dione of the general formula [I] and particularly the new derivatives of 3-hydrocinnamoyl-6-methyl-2H-pyran-2,4(3H)-dione of the formula [Ia] may be readily prepared by a process comprising two successive steps, i.e., a first step of subjecting 3-acetyl-6-methyl-2H-pyran-2,4(3H)-dione [II] and a substituted or unsubstituted aldehyde [III] of the formula

Ar—CHO  [III]

wherein Ar is as defined above, to Claisen-Schmidt condensation in a known manner to give 3-cinnamoyl-6-methyl-2H-pyran-2,4(3H)-dione or a substituted derivative thereof [IV] of the formula:

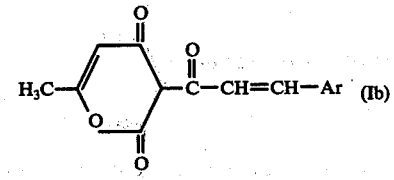

wherein Ar is as defined above, as the condensation product, and a second step of selectively hydrogenating this condensation product [IV] in a known manner to give the derivative of 0-methyl-2H-pyran-2,4(3H)-dione of the formula [I]. The starting materials of Formulae II and III are readily obtainable or can be prepared by conventional procedures, e.g. as described in "Chemical Abstracts" 50, 8619f.

This process may be shown by the following equation.

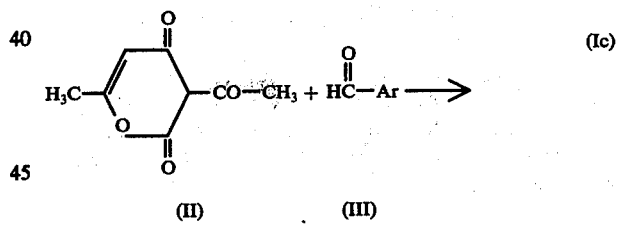

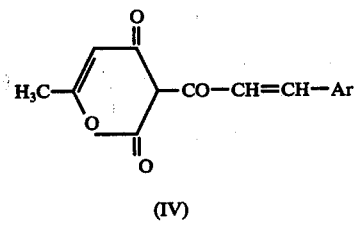

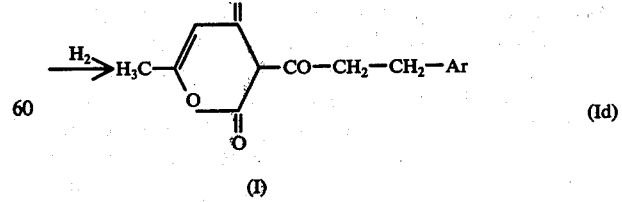

According to a second aspect of the present invention, therefore, there is provided a process for the production of derivatives of 6-methyl-2H-pyran-2,4(3H)-dione of the general formula:

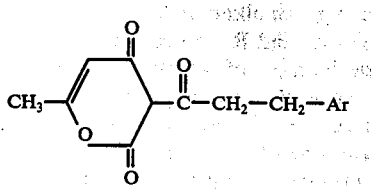

wherein Ar is as defined hereinbefore, which comprises subjecting a 3-acetyl-6-methyl-2H-pyran-2,4(3H)-dione of the formula:

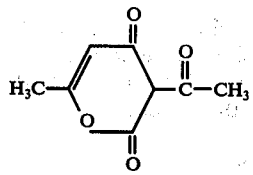

and an aldehyde of the formula:

Ar—CHO       [III]

wherein Ar is defined hereinbefore, to Claisen-Schmidt condensation in a known manner to give a derivative of 6-methyl-2H-pyran-2,4(3H)-dione of the formula

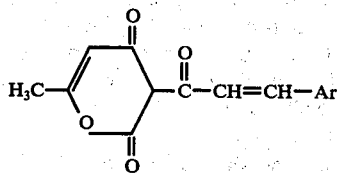

where Ar is as defined above as the condensation product, and then hydrogenating this condensation product [IV] in a known manner.

According to a particular embodiment of the second aspect of the present invention, there is further provided a process for the production of A derivative of 3-hydrocinnamoyl-6-methyl-2H-pyran-2,4(3H)-dione of the formula:

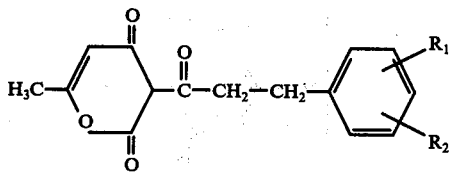

wherein $R_1$ and $R_2$ may be the same or different and are each a hydrogen atom, a halogen atom, hydroxyl, cyano, trifluoromethyl, a lower alkyl of 1–4 carbon atoms, a lower alkoxyl of 1–4 carbon atoms, carbamoyl — $CONH_2$, a substituted amino group —$NR'R''$ or an alkoxycarbonyl group —CO—OR ' where R' and R'' may be the same or different and are each lower alkyl of 1–4 carbon atoms; or alternatively $R_1$ and $R_2$ together form a chain —O—R'''—O— where R''' is a lower alkylene of 1–4 carbon atoms, which comprises subjecting 3-acetyl-6-methyl-2H-pyran 2,4(3H)-dione of the formula [II] and a substituted benzaldehyde of the formula:

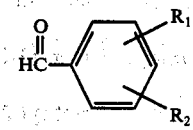

wherein $R_1$ and $R_2$ are as defined above, to Claisen-Schmidt condensation in a known manner to give a derivative of 3-cinnamoyl-6-methyl-2H-pyran-2,4(3H)-dione of the formula:

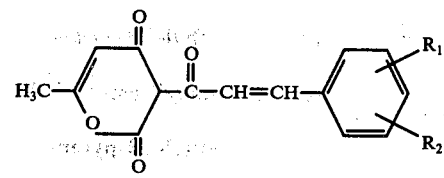

wherein $R_1$ and $R_2$ are as defined above, and then hydrogenating the resulting condensation product [IVa] selectively in a known manner.

In the process according to the second aspect of the present invention, the first step of condensing 3-acetyl-6-methyl-2H-pyran-2,4(3H)-dione [II] with an aldehyde of the formula [III] or particularly a substituted benzaldehyde of the formula [IIIa] may be carried out in a usual manner which is known as Claisen-Schmidt condensation. It is preferred that a molar proportion of 3-acetyl-6-methyl-2H-pyran-2,4(3H)-dione [II] is reacted with 0.1 to 10 molar proportions of the aldehyde [III] or [IIIa] in the presence of a condensation catalyst which may be a base. The condensation reaction may take place in an organic solvent in which the reagents and the catalyst are soluble and which is inert to the condensation reaction. In case the aromatic aldehyde reagent [III] or [IIIa] is in the form of a liquid, an excess of the aldehyde reagent may be used as the reaction medium or solvent. Suitable solvents are well known in the art and include but are not limited to methanol, ethanol, iso-propanol, tert-butanol, ethyl acetate, ethylene glycol, benzene, toluene, chloroform, methylene chloride, trichloroethylene, 1,2-dichloroethane, tetrahydrofuran, dioxan, dimethylsulfoxide (DMSO), dimethylformamide (DMF) and the like. The solvents can be used singly or in admixture of two or more. For the base which serves as the condensation catalyst, there may be used any of bases which are known to promote the Claisen-Schmidt condensation process. Suitable catalysts include but are not limited to organic amines, preferably a secondary amine, e.g. morpholine, piperidine, and pyrrolidine etc., and those primary amines such as cyclohexylamine which easily form a Schiff base with an aromatic aldehyde. The base as the catalyst can usually be used in an amount of 0.1 to mol. per mol. of the 3-acetyl-6-methyl-2H-pyran-2,4(3H)-dione [II]. The Claisen-Schmidt condensation step is preferably carried out at a reaction temperature which is in a range of room temperature to about 130° C., preferably 50°–100° C. In case the condensation reaction is effected at the temperatures higher than 130° C, the yield of the condensation product [IVa] is deteriorated mainly due to the formation of tarry products. The first step of the process generally gives high yields of a derivative of 3-cinnamoyl-6-methyl-2H-pyran-2,4(3H)-dione    IVa] which is usually a crystalline product of yellow color.

With respect to the aldehyde [III] or [IIIa] which is used as one of the starting materials for the first step of the process, it can be mono-substituted, di-substituted or multi-substituted on the aromatic or heterocyclic nucleus. Thus, the aldehyde [III] or [IIIa] can carry a substituent, for example, o-hydroxyl, m-hydroxyl, p-hydroxyl, o-methyl, p-methyl, o-methoxyl, m-methoxyl, p-methoxyl, o-chloro, m-chloro, p-chloro, o-fluoro, m-fluoro, p-fluoro, acetyloxy, p-methoxycarbonyl, p-carbamoyl, p-cyano, m-trifluoromethyl, p-(dimethyl) amino, etc., for either one of the substituents $R_1$ and $R_2$ on the aromatic or heterocyclic ring of the formula [III] or on the phenyl ring of the formula [IIIa]. The substituted benzaldehyde of the formula [IIIa] can also be di-substituted on the phenyl ring, e.g. by pairs of o-hydroxyl and m-methoxyl; m-chloro and p-chloro; m-hydroxyl and p-hydroxyl; m-hydroxyl and p-methoxyl; or a chain —$m$—O—$CH_2$—$p$—O— (i.e., 3,4-methylenedioxy) for both the substituents $R_1$ and $R_2$ on the phenyl ring thereof.

Since the condensation product [IV] or [IVa] can be obtained as salt of the β-dione with the base, it is generally desirable to treat the salt with a strong acid such as hydrochloric or sulfuric acid to afford the free form of the condensation product [IV] or ]IVa]. The intermediate condensation product [IV] or [IVa] which has been formed in the first step of the process is then subjected to hydrogenation in the second step of the process, so that it may be selectively converted into the corresponding dihydro derivatives of 6-methyl-2H-pyran-2,4(3H)-dione [I] or [Ib] as the final product. The hydrogenation which takes place in the second step of the process according to the second aspect of the present invention can be by any of the known hydrogenation methods which are suitable for converting the olefinic double bond present in the side-chain of the derivative of 3-cinnamoyl-6-methyl-2H-pyran-2,4(3H)-dione [IV] or [IVa] into a saturated covalent bond, as long as simultaneous hydrogenation of the β-dione group and the aromatic or heterocyclic ring, and particularly the double bond in the pyran ring of the derivative of 3-cinnamoyl-6-methyl-2-H-pyran-2,4(3H)-dione [IV] or [IVa] can be avoided. As it is well known that the sensitivity of an aromatic or heterocyclic ring, particularly phenyl ring, to hydrogenation is different from the sensitivity of the olefinic double bond to hydrogenation, it is easy for those skilled in the art to select a procedure and reaction conditions of the hydrogenation by which the olefinic double bond of the side-chain is preferentially or selectively hydrogenated into the saturated bond without affecting or hydrogenating the double bond of the pyran ring and the aromatic or heterocyclic ring.

To hydrogenate the intermediate condensation product [IV] or [IVa] selectively into the final product [I] or [Ib] in the second step of the process according to the second aspect of the present invention, the intermediate condensation product [IV] or [IVa] is preferably subjected to a catalytic hydrogenation which can normally be carried out at room temperature and atmospheric pressure in the presence of a usual hydrogenation catalyst, e.g., platinum, palladium, rhodium, Raney nickel, etc. Platinum, palladium and rhodium, etc. can be supported by a suitable carrier such as carbon or alumina, if desired. This catalytic hydrogenation is preferably effected in a solution of the intermediate condensation product [IV] or [IVa] in an organic solvent such as ethanol, tetrahydrofuran, dioxan and acetic acid etc. The hydrogenation catalyst is generally used in an amount of 0.01% by weight of the intermediate condensation product. The catalytic hydrogenation can be continued until one mol. equivalent of hydrogen is absorbed by the reaction mixture. When the hydrogenation has been completed, the reaction mixture is freed from the catalyst, e.g. by filtration, and then distilled to remove the solvent. In this way, the derivative of 6-methyl-2H-pyran-2,4(3H)-dione [I] or [Ib] is obtained in a substantially quantitative yield, and it then can be purified by recrystillization, silica gel chromatography, alumina chromatography or any other suitable purification method to give the final product in a pure state and in an excellent yield.

The new compounds of the general formula [I] and particularly of the formulae [Ia] and [Ib] according to the first aspect of the present invention are useful as hypotensive agents. They exhibit low toxicity and the biochemical properties of strongly inhibiting the action of tyrosine hydroxlase and dopamine β-hydroxylase, thus inhibiting in vivo the biosynthesis of norepinephrine as stated hereinabove.

The new compounds of the present invention have been examined for their biological activities, and their ihibition to tyrosine hydroxylase and dopamine β-hydroxylase are summarized below in Table 2. The details of the test methods used and the close relationship and reliable correlation of biological activities between in vitro and in vivo test results are well documented in the literature, e.g. J. Antibiot. 23: 514 (1970); Biochem. Pharmacol., 19: 35 (1970); and J. Am. Chem. Soc. 93: 1285 (1971). For instance, 3-(2-methoxyhydrocinnamoyl)-6-methyl-2H-pyran-2,4(3H)-dione, typical of the new compounds of the present invention, was tested by administering it to mice; the $LD_{50}$ was 1200 mg/kg. by intraperitoneal injection. When 160 mg/kg., 40 mg/kg., and 10 mg/kg. of 3-(2-methoxyhydrocinnamoyl)-6-methyl-2H-pyran-2,4(3H)-dione were orally or intraperitoneally given daily to mice for 30 days, none of the usual toxic signs appeared except a decrease in the blood pressure. The effects of this compound on tyrosine hydroxylase and dopamine β-hydroxylase were also tested by the methods described in the Journal of Antibiotics 23: 514 (1970) and Biochem. Pharmacol. 19: 35 (1970), respectively. In this test, the following inhibition % to tyrosine hydroxylase was observed at the following concentrations of 3(2-methoxyhydrocinnamoyl)-6-methyl-2H-pyran-2,4(3H)-dione:32% at 100 mcg/cc, 22% at 50 mcg/cc, 18% at 25 mcg/cc and 10% at 12.5 mcg/cc; the 50% inhibition concentration to dopamine β-hydroxylase was found to be 0.55 mcg/cc.

Hydroxylation of tyrosine is the rate-limiting step of norepinephrine biosynthesis. Therefore, inhibition of tyrosine hydroxylase results in inhibition of norepinephrine synthesis in vivo which results in lowering the blood pressure. The injection of a large dose (200 mg/kg of body weight) of 3-(2-methoxyhydrocinnamoyl)-6-methyl-2H-pyran-2,4(3H)-dione to mice and rats did not cause sleeping and a sedative effect was not recognized. Therefore, it is suggested that blood brain barrier inhibits penetration of this compound into the brain cells. Daily injection or daily oral administration of this compound to rats at a daily dosage of 3.5 mg/kg. of body weight lowered both the systolic and the diastolic blood pressure. The hypotensive effect can be seen even more markedly when it is administered to genetically hypertensive rats developed by Prof. Okamoto, of the Medical School, University of Kyoto, Japan, and described in "Journal of Antibiotics" 23; 514 (1970).

When 6.25 mg/kg was intraperitoneally injected to a rat of 185 mm. systolic blood pressure and another rat of 188 mm., the blood pressure was then lowered to 115–145 mm. and 138–166 mm. respectively during 1–22 hours after the injection. When 12.5 mm/kg. was intraperitoneally injected to a rat of 190 mm. systolic blood pressure, the pressure was reduced to 146–162 mm. during 1–22 hours after the injection. The oral administration of this compound daily (3.1 mg/kg., 6.25 mg/kg., 12.5 mg/kg, 25 mg/kg,) for three days showed marked reduction of blood pressure. It caused 20–30% reduction of blood pressure which continued for about 5 days after the last oral administration.

Thus, 3-(2-methoxyhydrocinnamoyl)-6-methyl-2H-pyran-2,4(3H)-dione inhibits tyrosine hydroxylase and dopamine β-hydroxylase and reduces blood pressure. 3-(2-methoxyhydrocinnamoyl)-6-methyl-2H-pyran-2,4(3H)-dione may be used in combination with other hypotensive agents such as reserpine.

According to a third aspect of the present invention therefore, there is provided a new hypotensive agent comprising a derivative of 6-methyl-2H-pyran-2,4(3H)-dione of the general formula [I] or [Ia] as defined above or particularly a derivative of 3-hydrocinnamoyl-6-methyl-2H-pyran-2,4(3H)dione of the formula [Ib] as defined above, as the active ingredient thereof. According to a further aspect of the present invention, there is also provided a new hypotensive agent comprising 3-hydrocinnamoyl-6-methyl-2H-pyran-2,4(3H)-dione or 3-(3,4-dimethoxyhydrocinnamoyl)-6-methyl-2H-pyran-2,4(3H)-dione as the active ingredient; these two known compounds have now been found to also be active in reducing blood pressure as stated hereinbefore. The new compound of the formula [I] or [Ia], particularly of the formula [Ib] according to the present invention, as well as the known compounds 3-hydrocinnamoyl-6-methyl-2H-pyran-2,4(3H)-dione and 3-(3,4-dimethoxyhydrocinnamoyl)-6-methyl-2H-pyran-2,4(3H)-dione can be administered in various ways, for example, orally, intravenously, and intrarectally.

Due to their tyrosine hydroxylase inhibiting activity, the compounds of this invention are useful as hypotensive agents in human and veterinary medicine. These compound are especially effective against essential hypertension (hyperpiesia) in adult humans.

The compounds of this invention can be employed in mixture with conventional excipients, i.e., pharmaceutically acceptable organic and inorganic carrier substances suitable for parenteral, enteral or topical application which do not deleteriously react with the active compounds. Suitable pharmaceutically acceptable carriers include but are not limited to water, salt solutions, alcohols, vegetable oils, polyethylene glycols, gelatine, lactose, amylose, magnesium stearate, talc, silicic acid, viscous paraffin, perfume oil, fatty acid monoglycerides and diglycerides, pentaerythritol fatty acid esters, hydroxy methylcellulose, polyvinyl pyrrolidone, etc. The pharmaceutical preparation can be sterilized and if desired mixed with auxiliary agents, e.g., lubricants, preservatives, stabilizers, wetting agents, emulsifiers, salts for influencing osmotic pressure, buffers, coloring, flavoring and/or aromatic substances and the like which do not deleteriously react with the active compounds.

For parenteral application, particularly suitable are solutions, preferably oily or aqueous solutions, as well as suspensions, emulsions, or implants, including suppositories. Ampoules are convenient unit dosages.

For enteral application, particularly suitable are tablets, dragees, or capsules having the talc and/or a carbohydrate carrier or binder or the like, the carrier preferably being lactose and/or corn starch and/or potato starch. A syrup, elixir or the like can be used wherein a sweetened vehicle is employed. Sustained release compositions can be formulated including those wherein the active compound is protected with differentially degradable coatings, e.g., by microencapsulation, multiple coatings, etc.

Generally, the compounds of this invention are dispensed in unit dosage form comprising 100 – 500 mg. of a pharmaceutical carrier per each unit dosage and the amount of active agent of the invention per unit dosage is about 10 to 100 mg.

The compounds of this invention are generally administered to animals, including but not limited to mammals, e.g., humans, livestock, household pets, etc.

Oral administration is preferred, the compounds of this invention being particularly valuable in the treatment of humans afflicted with essential hypertension. In this regard, they can be employed in substantially the same manner as known compounds such as α-methyl-3,4-oihydroxyphenylalamine.

A hypotensively effective daily dosage of the active compounds as administered orally to humans generally comprises about 30 to 1,000 preferably 30 to 500 mg/kg, together with 100–500 mg. of pharmaceutically acceptable carrier. The dose can be administered singly or as divided dosages throughout the day.

It will be appreciated that the actual preferred amounts of active compounds used will vary according to the specific compound being utilized, the particular compositions formulated, the mode of application, and the particular situs and organism being treated. Optimal application rates for a given set of conditions can be ascertained by those skilled in the art using conventional dosage determination tests in view of the above guidelines.

In addition to the use of these compounds for administration to mammals, they can be employed in admixture with carriers, germicides, fungicides, or soaps, etc., for use as antiseptic solutions and the like.

Without further elaboration, it is believed that one skilled in the art can, using the preceding description, utilize the present invention to its fullest extent. The following preferred specific embodiments are, therefore, to be construed as merely illustrative and not limitative of the remainder of the disclosure in any way whatsoever. In the following Examples, the temperatures are set forth uncorrected in degrees Celsius; unless otherwise indicated, parts and percentages are by weight. The values obtained in elemental analyses are within commonly accepted limits of error.

EXAMPLE 1

This example describes the production of 3-(4-methoxyhydrocinnamoyl)-6-methyl-2H-pyran-2,4(3H)-dione in two steps.

1. The preparation of 3-(4-methoxycinnamoyl)-6-methyl-2H-pyran-2,4(3H)-dione was conducted in the following way. A solution of 6.15 g. of dehydroacetic acid, namely 3-acetyl-6-methyl-2H-pyran-2,4(3H)-dione, 5.72 g. of anisaldehyde and 1.07 g. of piperidine dissolved in 50 ml. of chloroform was heated for 7.5 hours under reflux, while the water liberated was continuously removed during the reaction with anhydrous sodium sulfate. After the reaction, 100 ml. of chloroform was added and the combined organic layer was washed with dilute hydrochloric acid and water. The organic layer was dried over anhydrous sodium sulfate and the solvent was distilled off under reduced pressure. After recrystallization from dioxane, 4.76 g. of 3-(4-methoxycinnamoyl)-6-methyl-2H-pyran-2,4(3H)-dione was obtained as yellow crystals, showing mp. 205°–207° C.

| Elemental analysis | C(%) | H(%) |
|---|---|---|
| Found: | 67.19 | 5.15 |
| Calculated for $C_{16}H_{14}O_5$: | 67.12 | 4.93 |

2. The hydrogenation of 3-(4-methoxycinnamoyl)-6-methyl-2H-pyran-2,4(3H)-dione as prepared in the above step of Claisen-Schmidt condensation was carried out in the following way. 3-(4-Methoxycinnamoyl)-6-methyl-2H-pyran-2,4(3H)-dione (0.796 g.) was suspended in 100 ml. of tetrahydrofuran, and the hydrogenation was effected in the presence of 0.1 g of 5% platinum-charcoal at room temperature and under the atmospheric pressure.

One mole equivalent of hydrogen was absorbed in 6 hours. Upon removal of the catalyst and the solvent, yellow crystals were obtained. The crystals were subjected to silica gel chromatography for purification, affording pale-yellow crystals. Recrystallization from ethanol gave 0.579 g. of 3-(4-methoxyhydrocinnamoyl)-6-methyl-2H-pyran-2,4(3H)-dione of mp. 128–129° C.

| Elemental analysis | C(%) | H(%) |
|---|---|---|
| Found: | 66.42 | 5.70 |
| Calculated for $C_{16}H_{16}O_5$: | 66.66 | 5.59 |
| Inhibition (%) to Tyrosine Hydroxylase: | 47.9% at a concentration of 200 mcg/cc, 40.7% at a concentration of 100 mcg/cc. | |
| Inhibition (%) to Dopamine β-Hydroxylase: | 35% at a concentration of 200 mcg/cc. | |

EXAMPLE 2

This example illustrates the production of 3-(3-hydroxy-4-methoxyhydrocinnamoyl)-6-methyl-2H-pyran-2,4(3H)-dione in two steps.

1. The preparation of 3-(3-hydroxy-4-methoxycinnamoyl)-6-methyl-2H-pyran-2,4(3H)-dione was conducted in the following way. A solution of 13.3 g. of dehydroacetic acid, 11.9 g. of isovanillin and 2.0 g. of piperidine dissolved in 160 ml. of chloroform was heated for 3.5 hours under reflux, while the water liberated was continuously removed during the reaction in the same manner as given in Example 1. After the reaction, crystals deposited were collected by filtration. Upon recrystallization from a mixed solvent of ethanol and dioxane, 9.78 g. of 3-(3-hydroxy-4-methoxycinnamoyl)-6-methyl-2H-pyran-2,4(3H)-dione was obtained as yellow crystals of mp. 217°–219° C.

| Elemental analysis | C(%) | H(%) |
|---|---|---|
| Found: | 63.34 | 4.67 |
| Calculated for $C_{16}H_{14}O_6$: | 63.57 | 4.67 |

2. The hydrogenation of 3-(3-hydroxy-4-methyoxycinnamoyl)-6-methyl-2H-pyran-2,4(3H)-dione as prepared in the above step of Claisen-Schmidt condensation was carried out in the following way. The condensation product (1.39 g.) obtained in the above step was dissolved in 150 ml. of dioxane, and the hydrogenation was effected in the presence of 0.1 g. of 5% palladium-charcoal at room temperature and under the atmospheric pressure. One mole equivalent of hydrogen was absorbed in 8 hours. After removal of the catalyst and the solvent, the remaining crystalline product was subjected to silica gel chromatography for purification. Upon recrystallization from a mixed solvent of ethanol and n-hexane, 1.11 g. of 3-(3-hydroxy-4-methoxyhydrocinnamoyl)-6-methyl-2H-pyran-2,4(3H)-dione was obtained, showing mp. 115–116° C.

| Elemental analysis | C(%) | H(%) |
|---|---|---|
| Found: | 62.96 | 5.11 |
| Calculated for $C_{16}H_{16}O_6$: | 63.15 | 5.30 |
| Inhibition (%) to Tyrosine Hydroxylase: | 93.9% at a concentration of 200 mcg/cc, 80.8% at a concentration of 100 mcg/cc. | |
| Inhibition (%) to Dopamine β-hydroxylase: | 67% at a concentration of 200 mcg/cc. | |

EXAMPLE 3

This example illustrates the production of 3-(3,4-methylenedioxyhydrocinnamoyl)-6-methyl-2H-pyran-2,4(3H)-dione in two steps.

1. The preparation of 3-(3,4-methylenedioxycinnamoyl)-6-methyl-2H-pyran-2,4(3H)-dione was conducted in the following way. A solution of 18.6 g. of dehydroacetic acid 17.1 g. of piperonal and 3.04 g. of piperidine dissolved in 220 ml. of chloroform was refluxed for 20 hours, while the water liberated was continuously removed during the reaction with anhydrous sodium sulfate. After the reaction, the organic layer was washed with dilute hydrochloric acid and water followed by treatment with sodium sulfate, and the solvent was removed under reduced pressure.

The crystalline product obtained was recrystallized from dioxane-ethanol, affording 9.12 g. of 3-(3,4-methylenedioxycinnamoyl)-6-methyl-2H-pyran-2,4(3H)-dione, mp. 197°–198° C.

| Elemental analysis | C(%) | H(%) |
|---|---|---|
| Found: | 64.10 | 4.17 |
| Calculated for $C_{16}H_{12}O_6$: | 64.00 | 4.03 |

2. The hydrogenation of 3-(3,4-methylenedioxy-cinnamoyl)-6-methyl-2H-pyran-2,4(3H)-dione as prepared in the above step of Claisen-Schmidt condensation was carried out in the following way.

The condensation product 4.05 g) was dissolved in 200 ml. of tetrahydrofuran and the hydrogenation was effected in the presence of 0.3 g. of 5% palladium-charcoal at room temperature and under the atmospheric pressure. One mole equivalent of hydrogen was absorbed in 5 hours. After removal of the catalyst and the solvent, the residue was recrystallized from ethanol, affording 2.14 g. of 3-(3,4-methylenedioxy-hydrocinnamoyl)-6-methyl-2H-pyran-2,4(3H)-dione, mp. 103–104° C.

| Elemental analysis | C(%) | H(%) |
|---|---|---|
| Found: | 63.50 | 4.71 |

-continued

| Elemental analysis | C(%) | H(%) |
|---|---|---|
| Calculated for $C_{16}H_{14}O_6$: | 63.57 | 4.67 |

Inhibition (%) to
Tyrosine Hydroxylase: 18.5% at a concentration of 200 mcg/cc, 13.7% at a concentration of 100 mcg/cc.
Inhibition (%) to
Dopamine $\beta$-Hydroxylase: 86.7% at a concentration of 200 mcg/cc.

EXAMPLES 4–39

In these examples, various derivatives of 6-methyl-2H-pyran-2,4(3H)-dione of the formula [I] were prepared by condensing 3-acetyl-6-methyl-2H-pyran-2,4(3H)-dione [II] with various aldehydes of the formula [III] followed by catalytic hydrogenation of the condensation products in the same manner as the Claisen-Schmidt condensation step followed by hydrogenation step of Example 1.

The chemical structure of the products [I], solvent for hydrogenation and solvent for recrystallization are summarised in Table 1, and the yields of the products [I] are also shown in Table 1 together with their melting points, elemental analysis data, Inhibition (%) to tyrosine hydroxylase (TH) and Inhibition (%) to dopamine $\beta$-hydroxylase (DH) at different concentrations of the products [I] of 100 mcg/cc and 200 mcg/cc.

TABLE 1

| Example | Chemical structure | Solvent Hydrogenation | Recrystallization Solvent | Yield (%) of the product [I] | m.p. °C of the product [I] | Elementary analysis (%) | Inhibition (%) to TH/ concentration (mcg/cc) | Inhibition (%) to DH/ concentration (mcg/cc) |
|---|---|---|---|---|---|---|---|---|
| 4 | (structure with -OH phenyl) | Tetrahydrofuran | Ethanol n-hexane | 80 | 112–113 | Found: C 65.62, H 5.21 Calcd. for $C_{15}H_{14}O_5$: C 65.69, H 5.15 | 67.2/200 64.7/100 | 81.7/200 |
| 5 | (structure with -Cl phenyl) | " | Ethanol n-hexane | 81 | 111–112 | Found: C 61.41, H 4.48, Cl 12.00 Calcd. for $C_{15}H_{13}O_4Cl$: C 61.54, H 4.48, Cl 12.11 | 64.8/200 66.0/100 | 84.4/200 |
| 6 | (structure with di-Cl phenyl) | " | Ethanol | 79 | 120–121 | Found: C 55.07, H 3.80, Cl 21.73 Calcd. for $C_{15}H_{12}O_4Cl_2$: C 55.06, H 3.70, Cl 21.68 | 61.0/200 54.6/100 | 90.4/200 |
| 7 | (structure with -OH phenyl) | " | Dioxan-ethanol | 78 | 180–183 | Found: C 65.56, H 5.30 Calcd. for $C_{15}H_{14}O_5$: C 65.69, H 5.15 | 70.6/200 65.2/100 | 77.7/200 |
| 8 | (structure with -CN phenyl) | Dioxan | Ethanol | 62 | 155–157 | Found: C 67.88, H 4.78, N 4.68 Calcd. for $C_{16}H_{13}O_4N$: C 67.84, H 4.63, N 4.95 | 84.5/200 81.4/100 | 77.5/200 |
| 9 | (structure with di-OH phenyl) | " | Ethanol-chloroform | 60 | 170–173 | Found: C 61.92, H 4.91 Calcd. for $C_{15}H_{14}O_6$: C 62.16, H 4.86 | 93.5/200 80.6/100 | 20.6/200 |

TABLE 1-continued

| Example | Chemical structure | Solvent Hydrogenation | Recrystallization Solvent | Yield (%) of the product [I] | m.p. °C of the product [I] | Elementary analysis (%) | Inhibition (%) to TH/ concentration (mcg/cc) | Inhibition (%) to DH/ concentration (mcg/cc) |
|---|---|---|---|---|---|---|---|---|
| 10 | (structure with 3-Cl phenyl) | Tetrahydrofuran | Benzene-n-hexane | 82 | 96–98 | Found: C 61.81, H 4.39, Cl 12.01<br>Calcd. for $C_{15}H_{13}O_4Cl$: C 61.54, H 4.48, Cl 12.11 | 26.5/200<br>12.7/100 | 95.0/200 |
| 11 | (structure with 4-$OC_2H_5$ phenyl) | " | Ethanol | 72 | 125–126 | Found: C 67.32, H 6.23<br>Calcd. for $C_{17}H_{19}O_5$: C 67.54, H 6.00 | 10.1/200 | 6.0/200 |
| 12 | (structure with $(CH_2)_4$-phenyl) | " | Ethanol-n-hexane | 72 | 92–93 | Found: C 71.51, H 6.27<br>Calcd. for $C_{17}H_{18}O_4$: C 71.31, H 6.34 | 33.7/100 | 85.8/200 |
| 13 | (structure with OH-phenyl) | " | Methanol | 50 | 154–156 | Found: C 65.57, H 5.21<br>Calcd. for $C_{15}H_{14}O_5$: C 65.59, H 5.15 | 59.5/200<br>44.4/100 | 52.5/200 |
| 14 | (structure with $COOCH_3$-phenyl) | " | Methanol | 55 | 123–124 | Found: C 64.49, H 5.16<br>Calcd. for $C_{17}H_{16}O_6$: C 64.55, H 5.10 | 15.0/200<br>13.0/100 | 54.9/200 |
| 15 | (structure with HO, $OCH_3$-phenyl) | " | Methanol | 46 | 134–135 | Found: C 63.12, H 5.42<br>Calcd. for $C_{16}H_{16}O_6$: C 63.15, H 5.30 | 20.9/100 | 29.9/200 |
| 16 | (structure with $N(CH_3)_2$-phenyl) | " | Methanol | 44 | 114–115 | Found: C 67.56, H 6.38, N 4.46<br>Calcd. for $C_{17}H_{19}O_4N$: C 67.76, H 6.36, N 4.65 | 23.0/100 | 26.1/200 |
| 17 | (structure with 2-Cl phenyl) | " | Ethanol-ether | 62 | 100–102 | Found: C 61.77, H 4.51, Cl 11.71<br>Calcd. for $C_{15}H_{13}O_4Cl$: C 61.54, H 4.48, Cl 12.11 | 48.4/200<br>37.1/100 | 89.8/200 |

TABLE 1-continued

| Example | Chemical structure | Solvent Hydrogenation | Recrystallization Solvent | Yield (%) of the product [I] | m.p. °C of the product [I] | Elementary analysis (%) | Inhibition (%) to TH/ concentration (mcg/cc) | Inhibition (%) to DH/ concentration (mcg/cc) |
|---|---|---|---|---|---|---|---|---|
| 18 | 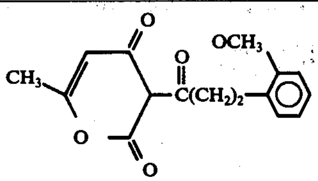 | Dioxan | Dioxan-ether | 81 | 151–154 | Found: C 66.58, H 5.71 Calcd. for $C_{16}H_{16}O_5$: C 66.66, H 5.59 | 32.0/100 | 98.3/200 |
| 19 | 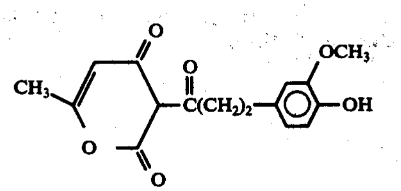 | Ethanol | Ethanol-n-hexane | 49 | 145–147 | Found: C 63.16, H 5.42 Calcd. for $C_{16}H_{16}O_6$: C 63.15, H 5.30 | 26.0/200 14.6/100 | 29.6/200 |
| 20 | 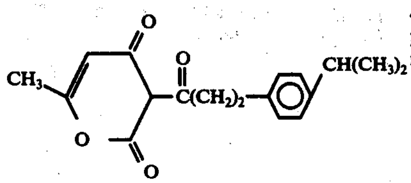 | Tetrahydrofuran | Ethanol-n-hexane | 57 | 79–81 | Found: C 71.96, H 6.89 Calcd. for $C_{18}H_{20}O_4$: C 71.98, H 6.71 | 25.5/200 16.8/100 | 94.5/200 |
| 21 | 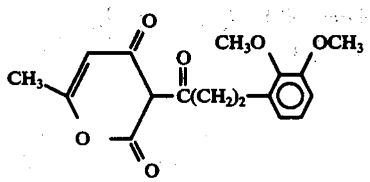 | " | Ethanol-n-hexane | 54 | 99–102 | Found: C 64.16, H 5.72 Calcd. for $C_{17}H_{18}O_6$: C 64.14, H 5.70 | 39.0/100 | 74.7/200 |
| 22 | 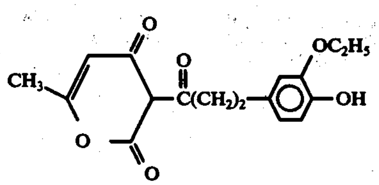 | Dioxan | Ethanol-n-hexane | 37 | 115–118 | Found: C 64.13, H 5.86 Calcd. for $C_{17}H_{18}O_6$: C 64.14, H 5.70 | 24.4/200 22.7/100 | 61.5/200 |
| 23 | 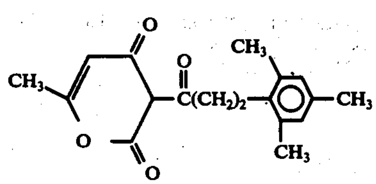 | Tetrahydrofuran | Ethanol-chloroform | 80 | 135–136 | Found: C 71.87, H 6.77 Calcd. for $C_{18}H_{20}O_4$: C 71.98, H 6.71 | 8.7/100 | 28.9/200 |
| 24 | 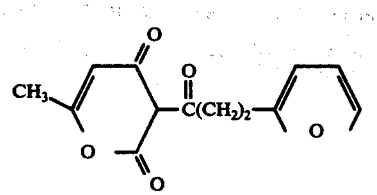 | " | Ether-peroleum ether | 30 | 98–99 | Found: C 62.87, H 4.84 Calcd. for $C_{13}H_{12}O_5$: C 62.90, H 4.87 | 45.5/200 44.7/100 | 60.3/200 |
| 25 | 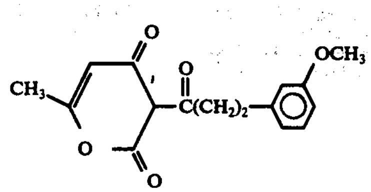 | 0.6% Sodium hydroxide ethanol solution | Ethanol | 65 | 87–88 | Found: C 66.63, H 5.72 Calcd. for $C_{16}H_{16}O_5$: C 66.66, H 5.59 | 34.9/200 32.0/100 | 83.5/200 |

TABLE 1-continued

| Example | Chemical structure | Solvent Hydrogenation | Recrystallization Solvent | Yield (%) of the product [I] | m.p. °C of the product [I] | Elementary analysis (%) | Inhibition (%) to TH/ concentration (mcg/cc) | Inhibition (%) to DH/ concentration (mcg/cc) |
|---|---|---|---|---|---|---|---|---|
| 26 | (structure with Br phenyl) | Tetrahydrofuran | Ethanol-n-hexane | 30 | 79–80 | Found: C 53.60, H 3.80, N 23.54<br>Calcd. for $C_{15}H_{13}O_4Br$: C 53.43, H 3.89, N 23.70 | 19.8/200<br>11.3/100 | 97.0/200 |
| 27 | (structure with 3,4-dimethoxyphenyl) | 0.5% Sodium hydroxide ethanol solution | Dioxanethanol | 81 | 150–152 | Found: C 64.28, H 5.71<br>Calcd. for $C_{17}H_{18}O_6$: C 64.14, H 5.70 | 26.0/200<br>20.0/100 | 44.9/200 |
| 28 | (structure with 2,4-dichlorophenyl) | Tetrahydrofuran | Ethanol | 71 | 119–121 | Found: C 55.31, H 3.85, Cl 21.50<br>Calcd. for $C_{15}H_{12}O_4Cl_2$: C 55.06, H 3.70, Cl 21.68 | 29.1/200<br>29.8/100 | 100/200 |
| 29 | (structure with 4-methylphenyl) | " | Ether-n-hexane | 76 | 94–96 | Found: C 70.58, H 6.02<br>Calcd. for $C_{16}H_{16}O_4$: C 70.57, H 5.92 | 52.6/200<br>52.5/100 | 85/200 |
| 30 | (structure with methylfuryl) | 1% Sodium hydroxide ethanol solution | So-Ethanol-n-hexane | 18 | 79–80 | Found: C 64.23, H 5.27<br>Calcd. for $C_{14}H_{14}O_5$: C 64.11, H 5.38 | 23.5/100 | 100/200 |
| 31 | (structure with 4-F phenyl) | Tetrahydrofuran | Ethanol-n-hexane | 82 | 101–102 | Found: C 65.41, H 4.82, F 7.01<br>Calcd. for $C_{15}H_{13}O_4F$: C 65.22, H 4.74, F 6.88 | 60.1/100 | 42/200 |
| 32 | (structure with 4-CF$_3$ phenyl) | Tetrahydrofuran | Ethanol n-hexane | 78 | 97–99 | Found: C 58.92, H 4.10, F 17.60<br>Calcd. for $C_{16}H_{13}O_4F_3$: C 58.90, H 4.02, F 17.47 | 50.4/100 | 88/200 |
| 33 | (structure with 4-CONH$_2$ phenyl) | " | Ethanol | 65 | 175–177 | Found: C 63.91, H 5.04, N 4.72<br>Calcd. for $C_{16}H_{15}O_5N$: C 63.78, H 5.02, N 4.65 | 20.5/100 | 30.3/200 |

TABLE 1-continued

| Example | Chemical structure | Solvent Hydrogenation | Recrystalization Solvent | Yield (%) of the product [I] | m.p. °C of the product [I] | Elementary analysis (%) | Inhibition (%) to TH/concentration (mcg/cc) | Inhibition (%) to DH/concentration (mcg/cc) |
|---|---|---|---|---|---|---|---|---|
| 34 | [structure: CH₃ pyranedione with -C(CH₂)₂- linked to dichloro-hydroxyphenyl] | Dioxan | Ethanol | 75 | 184–186 | Found: C 52.62, H 3.61, Cl 20.48 Calcd.for C₁₅H₁₂O₅Cl₂: C 52.50, H 3.52, Cl 20.67 | 69.3/200 53.6/100 | 82.3/200 |
| 35 | [structure: CH₃ pyranedione with -C(CH₂)₂- linked to dimethoxy-hydroxyphenyl] | Tetrahydrofuran | Dioxan ethanol | 88 | 210–212 | Found: C 61.29, H 5.49 Calcd. for C₁₇H₁₈O₇: C 61.07, H 5.43 | 45.8/100 | 43.6/200 |
| 36 | [structure: CH₃ pyranedione with -C(CH₂)₂- linked to naphthyl] | " | Ethanol | 76 | 153–155 | Found: C 73.89, H 5.20 Calcd. for C₁₉H₁₆O₄: C 74.01, H 5.23 | 34.8/100 | 56.2/200 |
| 37 | [structure: CH₃ pyranedione with -C(CH₂)₂- linked to hydroxynaphthyl] | Dioxan | Dioxan ethanol | 54 | 203–215 | Found: C 70.27, H 4.82 Calcd. for C₁₉H₁₆O₅: C 70.36, H 4.93 | 57.2/200 41.8/100 | 44.7/200 |
| 38 | [structure: CH₃ pyranedione with -C(CH₂)₂- linked to thiophene] | Tetrahydrofuran | Ethanol | 32 | 87–89 | Found: C 59.22, H 5.63, S 12.24 Calcd.for C₁₃H₁₂O₄S: C 59.08, H 4.58, S 12.13 | 52.3/100 | 30.3/200 |
| 39 | [structure: CH₃ pyranedione with -C(CH₂)₂- linked to pyrrole (NH)] | Acetic acid | Ethanol | 48 | 180–182 | Found: C 63.21, H 5.24, N 5.81 Calcd.for C₁₃H₁₃O₄N: C 63.15, H 5.30, N 5.67 | 30.9/100 | 25.1/200 |

It is added that 3-hydrocinnamoyl-6-methyl-2H-pyran-2,4(3H)-dione exhibits inhibition to TH of 52.8% at 200 mcg/cc and 49.7% at 100 mcg/cc., and exhibits inhibition to DH of 100% at 100 mcg/cc., and that 3-(3,4-dimethoxyhydrocinnamoyl)-6-methyl-2H-pyran-2,4(3H)-dione exhibits inhibition to TH of 72.5% at 200 mcg/cc and 61.3% at 100 mcg/cc. and exhibits inhibition to DH of 32.5% at 200 mcg/cc.

EXAMPLE 40

The follwing materials:
3-(2-methoxylhydrocinnamoyl)-6-methyl-2H-pyran-2,4(3H)-dione: 100 g. Lactose: 500 g.

were well mixed together and ground, and the powdery mixture was formulated into 1000 capsules, each capsule containing 100 mg. of the active compound.

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A pharmaceutical composition suitable for use in treating essential hypertension in adult humans comprising a hypotensively effective amount of an agent selected from the group consisting of 6-methyl-2H-pyran-2,4(3H)-diones of the formula:

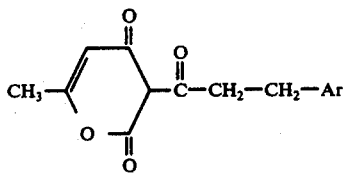

wherein Ar is phenyl substituted by at least one member selected from the group consisting of halogen, hydroxyl, trifluoromethyl, alkyl of 1-4 carbon atoms, alkoxy of 1-4 carbon atoms and alkylenedioxy of the formula —O—R'''—O— wherein R''' is alkylene of 1—4 carbon atoms, provided that said substituted phenyl is not 3,4-dimethoxyphenyl; and the physiologically acceptable salts thereof in combination with a pharmaceutically acceptable carrier.

2. A pharmaceutical composition according to claim 1, wherein said agent is selected from the group consisting of 6-methyl-2H-pyran-2,4(3H)-diones of the formula:

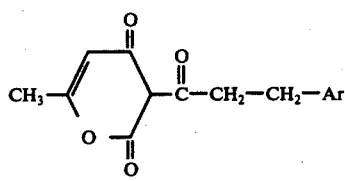

wherein Ar is phenyl substituted by at least one member selected from the group consisting of halogen, hydroxyl, alkyl of 1-4 carbon atoms and alkoxy of 1-4 carbon atoms, provided that said substituted phenyl is not 3,4-dimethoxyphenyl, and the physiologically acceptable salts thereof.

3. A process for treating essential hypertension in living animals which comprises administering a hypotensively effective amount of an agent selected from the group consisting of 6-methyl-2H-pyran-2,4(3H)-diones of the formula:

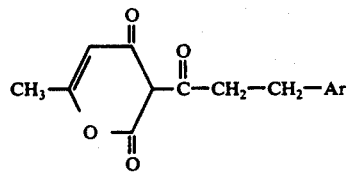

wherein Ar is phenyl substituted by at least one member selected from the group consisting of halogen, hydroxyl, trifluoromethyl, alkyl of 1-4 carbon atoms, alkoxy of 1-4 carbon atoms, and alkylenedioxy of the formula —O—R'''—O— wherein R''' is alkylene of 1-4 carbon atoms, provided that said substituted phenyl is not 3,4-dimethoxyphenyl; and the physiologically acceptable salts thereof to an animal afflicted with essential hypertension.

4. A process according to claim 3, wherein said agent is selected from the group consisting of 6-methyl-2H-pyran-2,4(3H)-diones of the formula:

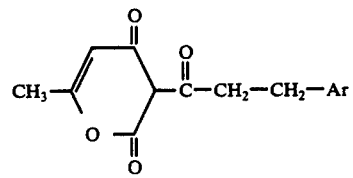

wherein Ar is phenyl substituted by at least one member selected from the group consisting of halogen, hydroxyl, alkyl of 1-4 carbon atoms and alkoxy of 1-4 carbon atoms, provided that said substituted phyenyl is not 3,4-dimethoxyphenyl, and the physiologically acceptable salts thereof.

5. A process according to claim 3, wherein said agent is selected from the group consisting of 3-hydrocinnamoyl-6-methyl-2H-pyran-2,4(3H)-dione; 3-(3,4-dimethoxyhydrocinnamoyl)-6-methyl-2H-pyran-2,4(3H)-dione; and the physiologically acceptable salts thereof.

6. A process according to claim 3, wherein said compound is one in which Ar is phenyl mono-substituted by chlorine, hydroxy, alkyl of 1-4 carbon atoms or alkoxy of 1-4 carbon atoms.

7. A process according to claim 3, wherein said compound is one in which Ar is di-substituted phenyl of the formula:

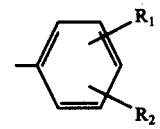

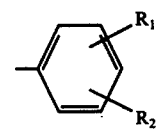

wherein $R_1$ and $R_2$ are each independently chlorine, hydroxy or lower alkoxy of 1-4 carbon atoms.

8. A process according to claim 3, wherein said compound is one in which Ar is phenyl substituted by at least one chlorine.

9. A process according to claim 3, wherein said compound is selected from the group consisting of 3-(4-chlorohydrocinnamoyl)-6-methyl-2H-pyran-2,4(3H)-dione and the physiologically acceptable salts thereof.

10. A process according to claim 3, wherein said compound is one in which Ar is phenyl substituted by at least one hydroxy.

11. A process according to claim 10, wherein said compound is selected from the group consisting of 3-(3-hydroxyhydrocinnamoyl)-6-methyl-2H-pyran-2,4(3H)-dione and the physiologically acceptable salts thereof.

12. A process according to claim 3, wherein said compound is one in which Ar is phenyl substituted by at least one alkoxy of 1-4 carbon atoms.

13. A process according to claim 3, wherein said compound is one in which Ar is phenyl substituted by one hydroxy and by one alkoxy of 1-4 carbon atoms.

14. A process according to claim 13, wherein said compound is 3-(3-hydroxy-4-methoxyhydrocinnamoyl)-6-methyl-2H-pyran-2,4(3H)-dione or physiologically acceptable salt thereof.

* * * * *